United States Patent [19]

Barth

[11] 4,071,615

[45] * Jan. 31, 1978

[54] FLAVORED DENTIFRICE

[75] Inventor: Jordan B. Barth, East Brunswick, N.J.

[73] Assignee: Colgate Palmolive Company, New York, N.Y.

[ * ] Notice: The portion of the term of this patent subsequent to Feb. 17, 1993, has been disclaimed.

[21] Appl. No.: 623,180

[22] Filed: Oct. 16, 1975

Related U.S. Application Data

[62] Division of Ser. No. 502,043, Aug. 30, 1974, Pat. No. 3,939,261.

[51] Int. Cl.$^2$ .............................................. A61K 7/18
[52] U.S. Cl. ...................................... 424/52; 426/548
[58] Field of Search ...................... 426/548; 424/49–58

[56] References Cited

U.S. PATENT DOCUMENTS

| 1,484,415 | 2/1924 | Shepherd | 424/49 |
| 1,716,035 | 6/1929 | Donchi | 424/49 |
| 2,130,034 | 9/1938 | Schmidt | 424/49 |
| 2,955,985 | 10/1960 | Kuna | 424/52 |
| 2,991,229 | 7/1961 | Ivison | 424/49 |
| 3,087,821 | 4/1963 | Horowitz et al. | 424/49 |
| 3,282,792 | 11/1966 | Fiscella | 424/52 |
| 3,475,533 | 10/1969 | Mayrand | 424/57 |
| 3,492,131 | 1/1970 | Schlatter | 426/212 |
| 3,574,824 | 4/1971 | Echeandria et al. | 424/50 |
| 3,629,398 | 12/1971 | Schmitt | 424/52 |
| 3,642,491 | 2/1972 | Schlatter | 426/217 |
| 3,662,059 | 5/1972 | Wiesner et al. | 424/52 |
| 3,689,637 | 9/1972 | Pader | 424/52 |
| 3,703,578 | 11/1972 | Cella et al. | 424/49 |
| 3,711,604 | 1/1973 | Colodney et al. | 424/52 |
| 3,753,739 | 8/1973 | Cella et al. | 426/548 |
| 3,761,288 | 9/1973 | Glicksman et al. | 426/548 |
| 3,799,918 | 3/1974 | Mazur | 260/112.5 |
| 3,800,046 | 3/1974 | Schlatter | 426/548 |
| 3,801,563 | 4/1974 | Nakajima et al. | 260/112.5 |
| 3,868,472 | 2/1975 | Berg et al. | 426/342 |
| 3,885,028 | 5/1975 | Cella et al. | 424/52 |
| 3,906,090 | 9/1975 | Colodney | 424/52 |
| 3,911,104 | 10/1975 | Harrison | 424/52 |
| 3,922,369 | 11/1975 | Glickman et al. | 426/548 |
| 3,928,633 | 12/1975 | Shoaf et al. | 426/548 |

FOREIGN PATENT DOCUMENTS 2,306,909 8/1973 Germany.

OTHER PUBLICATIONS

Cloninger et al., *Science,* vol. 170, pp. 81 & 82, 1970.

*Primary Examiner*—Shep K. Rose
*Attorney, Agent, or Firm*—Steven J. Baron; Murray M. Grill; Herbert S. Sylvester

[57] ABSTRACT

There is disclosed a substantially anhydrous dentifrice which contains a dipeptide sweetener in combination with an acid anhydride. There is also disclosed a method of making the same.

17 Claims, No Drawings

FLAVORED DENTIFRICE

This is a divisional of application Ser. No. 502,043 filed Aug. 30, 1974 allowed as U.S. Pat. No. 3,939,261 the benefit of which filing date is claimed.

This invention relates to a novel dentifrice preparation, more particularly to a dentifrice in which the sweetening agent which heretofore suffered from rapid loss of sweetening upon aging in an aqueous dentifrice is stabilized by formulation into an anhydrous cream containing a food grade acid anhydride therein. The invention being in the nature of an anhydrous dentifrice is succestible to the addition of various water incompatible dentifrice additives, such as the present sweetener, certain enzymes, bleaching agents, fluorides and the like. The invention also relates to methods of producing the aforesaid dentifrice.

The incorporation of certain water incompatible dentifrice additives in ordinary hydrous toothpastes has not been possible because of the instability or inactivity of these substances in the presence of moisture. Some fluoride additives from insoluble salts with the other ingredients in the hydrous toothpastes, thus rendering them ineffective for protection against caries. With other therapeutic additives, difficulties involving production and storage are encountered. As a result, the marketing of toothpaste products containing certain of these additives has not been possible. Moreover, attempts to formulate anhydrous toothpastes to circumvent the water incompatibility problem have been generally unsuccessful from the standpoint of consumer acceptance of these products.

In addition to the problems inherent in an anhydrous cream there is the additional problem of compatibility of the flavors and sweeteners employed in dental formulations.

It has been observed that taste and flavor are perhaps the most important single aspects with respect to the consumer acceptance of a dentifrice formulation. The selection of acceptable sweetener and flavoring ingredients is therefore of significant importance in the formulation of a dentifrice. It has oftentimes been stated that the foregoing is both an art as well as a science. It is an art in the sense that it requires the blending of the various components with the sweetening agents such that the final composition contains a pleasing taste as well as in providing for a composition in which the sweetener is stable. It is the foregoing that has presented particular difficulties in incorporating sweetening agents into a dentifrice inasmuch as the former must be compatible with the latter and both must remain essentially unchanged over the shelf life of the product.

At the present time, there are relatively few sweeteners which are both currently available for use in dentifrices as well as generally acceptable for use therein. This need has stimulated the search for artificial sweetening agents which may be used as sugar substitutes. The first artificial sweetener approved for general use was saccharin. Saccharin is markedly sweeter than sucrose, having a potency of 250-350 times the latter, but it has been known to leave a bitter aftertaste. More recently, the sweetening property of cyclohexylsulfamic acid (cyclamate) and its sodium and calcium salts was discovered. Those substances are about 30 times as sweet as sucrose, but also suffer from certain disadvantages.

Other more exotic sweeteners though available are generally not acceptable for use in a dentifrice due to their stability problems vis-a-vis the various components in the dentifrice. Some of those sweeteners which do not have stability problems have the drawback that they are not suitable for use as a primary sweetener due to the unacceptable timelag prior to the onset of their sweetness and/or their associated side tastes.

A further consideration in formulating a dentifrice relates to the fact that the polishing agents employed therein are generally absorbent materials and therefore there may be a selective absorption onto the polishing agent of the sweetener with accompanying changes in physical form of the toothpaste, chemical changes and accordingly changes in overall flavor.

The sweetening agent contemplated herein is a dipeptide sweetener, which may be characterized by the following general formula:

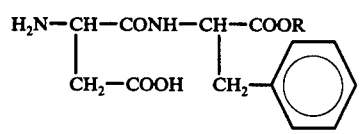

wherein R is an alkyl radical containing about 1 to 2 carbon atoms, preferably one.

Wherein R is 1, the dipeptide sweetener may be conveniently characterized as aspartylphenylanaline methyl ester.

The above sweetening agents are markedly sweeter than sucrose, possessing a potency of about 50-250 times relative to that standard. They are, moreover, lacking in the unpleasant aftertaste characteristic of currently available artificial sweeteners. The sweetening agents may be manufactured by the methods disclosed in U.S. Pat. No. 3,492,131, which is incorporated herein by reference.

The aforementioned dipeptide sweetening agents wherein R is methyl, i.e., the methyl esters, and the stereoisomers of L—L configuration are particularly preferred for incorporation into the instant dental formulation. L-aspartyl-L-phenylalanine methyl ester and L-aspartyl-L-hexahydrophenylalanine methyl ester thus display a potency of about 200-250 times that of sucrose. The corresponding ethyl esters are about half as sweet.

The above sweetener has heretofore been described in the literature and even peripherily mentioned for use in consumable toiletries such as mouthwashes and toothpaste by merely including same therein. Such dental products, however apparently never have been prepared, inasmuch as the literature is silent on the fact that the sweetener is not by itself stable in either an androus or aqueous dentifrice. The sweetness of the dipeptide sweetener has been found to rapidly dissipate soon (by shelf life standards) after incorporation into the dentifrice. It has been found that sweetness is rapidly lost in about one weeks time, the foregoing clearly unsatisfactory for a product that oftentimes has a shelf life of many months between factory packaging and ultimate consumer depletion of the product.

It has been unexpectedly found that following the teachings of the prior art leads to a product wherein the primary sweetness is rapidly lost and accordingly the dentifrice incorporating same no longer possesses a sufficient degree of sweetness to mask the associated side taste inherent in some dentifrices.

In order to incorporate same in a dentifrice there is the need to control the environment of this sweetener and accordingly, the dentifrice herein is substantially anhydrous; with this requirement, there is the accompanying need to incorporate an acid-anhydride or like material therein so as to maintain the stability and effectiveness of the sweetener and be operative to combine with free water present in the raw materials. It is understood that the acid anhydride will be non-toxic and suitable for oral use. It is also to be understood that other suitable acid functional materials may be employed, the principal guide-line being that they be substantially anhydrous.

It is accordingly an object of this invention to provide for a substantially anhydrous dentifrice containing a dipeptide sweetening agent.

It is another object of the invention to avoid one or more drawbacks of the prior art.

Broadly speaking, the invention includes the provision of a substantially anhydrous dentifrice which contains a dipeptide sweetener in admixture with an acid-anhydride.

The dipeptide esters contemplated herein are conveniently manufactured by methods suitable for the coupling of amino acids. An especially preferred starting material is the asparic acid derivative wherein the amino function is protected by a benzyloxycarbonyl group and the B-carboxy function by a benzyl ester group, and the α-carboxy group is converted to a p-nitrophenyl ester function. The preparation of that substance, i.e., N-benzoyloxy carbonyl-L-aspartic acid α-p-nitrophenyl, B-benzyl diester, is described by S. Guttmann *Helv. Chim. Acta,* 44 721 (1961).

The sweetening property of the dipeptide substances is partially dependent upon the stereochemistry of the individual amino acids, i.e., aspartic acid and phenylalamine, from which the dipeptides are derived. Each of the amino acids can exist in either the D or L form, but it has been determined that the L-aspartyl-L-phenylalamine esters are sweet while the corresponding D—D, D—L, and L—D isomers are not. Combinations of isomers which contain the L—L dipeptide, i.e., DL-aspartyl-L-phenylalamine, L-aspartyl-DL-phenylalamine and DL-aspartyl-DL-phenylalamine, are sweet also.

Combinations of the dipeptide sweetening agents with sugar or synthetic sweeteners such as saccharin likewise can be incorporated into dental formulations of this invention. Lesser amounts of each sweetener are, furthermore, required as a result of the effect by such combination.

Toothpastes or creams whether dispensed from flexible or resilient tubes or from pressurized containers, such as "aerosol" dispensers, will normally comprise polishing agents (s), vehicle (s), surface active agent(s) or detergents(s), gelling agent(s), and various other adjuvants, such as flavors, colorants, bactericides, tooth hardeners, e.g., fluorides or fluorine compounds, and preservatives or stabilizers.

Paste or cream dentifrices may be based in aqueous or substantially non-aqueous systems. The former, not included herein, will usually include substantial proportions of finely divided, solid polishing agent, surface active agent, gelling agent and some non-aqueous vehicle, e.g., glycerol, whereas the latter type will often contain a minor proportion of a particulate solid polishing agent, a larger proportion of non-aqueous vehicle, surface active agent and gelling agent, with a minor proportion of water unavoidably often being present in the raw materials.

The substantially anhydrous base of this invention is preferably formulated from the following: (1) humectant or an oil; (2) a non-toxic emulsifier; (3) gelling or binding agent; (4) an abrasive or abrasive-free inert ingredient; (5) standard toothpaste additives; and optionally, (6) water incompatible dentifrice additives.

The above-mentioned ingredients must, of course, be non-toxic and substantially anhydrous.

The dentifrice formulation of this invention includes liquids and solids that are proportioned as further defined hereinafter to form a creamy mass of desired consistency which is extrudable from an aerosol container or a collapsible tube (for example aluminum or lead). In general, the liquids in the dental cream will comprise chiefly glycerin or an oil, propylene glycol, polyethylene glycol 400, etc., including suitable mixtures thereof. It is advantageous usually to use a mixture of both humectant and binder such as glycerine and Carbowax 600. The total liquid content will generally be about 20 to 75 percent by weight of the formulation. It is preferred to use also a gelling agent in dental creams and gels such as the natural and synthetic gums and gum-like materials, for example, Irish moss, gum tragacanth, methyl cellulose, polyvinylpyrrolidone, hydrophilic colloidal carboxyvinyl polymers, such as those sold under the trademark Carbopol 934 and 940 and synthetic silicated clays such as those sold under the trademark Laponite CP and Laponite SP. These grades of Laponite have the formula

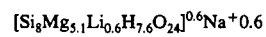

The solid portion of the vehicle is usually present in an amount of up to about 10 percent preferably about 0.2 to 5 percent by weight of the formulation.

The proportions of gelating agents or thickeners in the present dentifrices are sufficient to form an extrudable, shape-retaining product which can be squeezed from a tube onto a toothbrush and will not fall between the bristles of the brush but rather, will substantially maintain its shape thereon. In almost all cases no more than about 10% of gelling agent need be used and in most instances about 0.5 to 10% will suffice, with the preferred range, especially applicable to sodium carboxymethyl cellulose, being from 0.5 to 1.5%.

Suitable oils for use in the practice of this invention include those which have viscosity ranging from about 100 to about 300 centipoises at 70° F., and can be mineral oil, light liquid petrolatum thickened to the necessary viscosity; and vegetable oils. The preferred mineral oil is Mineral Oil U.S.P. (also known as Liquid Petrolatum U.S.P., mineral oil (heavy medicinal), white mineral oil, liquid paraffin, and heavy liquid petrolatum). Mineral oil U.S.P. is defined in *Remington's Pharmaceutical Sciences,* 13th. edition, Mack Publishing Co., Easton, Pa. 1965 as "a mixture of liquid hydrocarbons obtained from petroleum; a colorless, transparent, oily liquid, free or nearly free from fluorescene. It is tasteless and odorless when cold and develops not more than a faint odor of petroleum when heated."

The preferred light liquid petrolatum is Light Liquid Petrolatum N.F. also known as light liquid paraffin and light white mineral oil. It is described in *Remington's Pharmaceutical Science,* as ". . . a mixture of liquid hydrocarbons obtained from petroleum, it may contain a stabilizer." If the Light Liquid Petrolatum N.F. is used as the oil it must be thickened to the required viscosity of from about 100 to about 300 centipoises at 70° F. with one of the well-known commercially available inert thickening materials, such as a pyrogenic silica sold under the trademark CAB-O-SIL, or a hydrogenated castor oil, sold under the tradename THIXIN.

Suitable vegetable oils which may be used as the oil ingredient include coconut oil, cotton-seed oil, sesame oil and similar non-toxic vegetable oils, as described in *Vegetable Fats and Oils* by E. W. Eckey, Reinhold Publishing Corp., New York, 1954. The vegetable oil selected must, of course, fall within the required viscosity range of from about 100 to about 300 centipoises. A particular vegetable oil falling within this range is NEOBFE M-5, a fractional triglyceride of coconut oil. It is desirable that the vegetable oil ingredient contain a minor amount of an antioxidant such as butylated hydroxyanisole or butylated hydroxytoluene, preferably in an amount ranging from about 0.1 to about 3% by weight, based on the weight of the vegetable oil employed.

The liquid vehicle of the dentifrice, together with the gelling agent(s) and other constituents, forms an extrudable mass of a non-dripping consistency when extruded from a collapsible tube, such as an aluminum or lead tube. Thus, by the addition of more vehicle, the dental cream can be thinned and conversely, by the addition of more solids, especially more gelling agents, the products can be thickened. In most dentifrices, the liquid portion comprises glycerine; although it is preferred to employ glycerol, other suitable vehicles in place thereof or in addition thereto may also be present, either with the mentioned polyhydric alcohols or in replacement for them. Thus, propylene glycol, polyethylene glycol, mannitol and polypropylene glycol may be employed providing that they are physiologically acceptable and produce products having a desired refractive index, in the case of manufacture of visually clear dentifrices. Normally, the proportion of vehicle is determined by the physical properties of the extrudate. Usually, however, from about 10 to 90% of the vehicle will be employed, with about 10 to 35% being a typical range for production of opaque dentifrices and about 40 to 90% being useful for the manufacture of clear dental preparations.

It is to be understood that while ordinarily where sorbitol is employed in a dentifrice, it is used as an aqueous solution, sorbitol may be employed herein, with the proviso, however, that it be substantially anhydrous (i.e., crystaline).

It is to be understood that the substantially anhydrous system refers to the absence of sufficient free water to substantially adversely affect the stability of the sweetener. There may be present relatively minor proportions of water, or water in bound form or the like which are compatible in the system. Preferred ranges are, respectively, about 15 to 30% of the polyhydric alcohols for the opaque dentifrices and about 50 to 75% in the clear products.

In the preparation of tooth powders, it is usually sufficient to admix mechanically, e.g., by milling, the various solid ingredients, in appropriate quantities and particle sizes, and thereafter carrying out procedures known in the art for containerization of the product.

In chewable dental tablets the solids and liquids are proportioned similarly to the amounts in dental creams and the flavor is blended with the solids and liquids, a waxy matrix such as polyethylene glycol having a molecular weight of about 6,000 by weight, generally in amount of about 4-20 percent by weight, in order to facilitate forming a tablet or desired size and shape.

In addition, the formulation will generally include a dentally acceptable, substantially water insoluble, polishing agent of the type commonly employed in dental creams. The polishing agents are usually finely divided water insoluble powdered materials of particle sizes such that they pass a 140 mesh screen, U.S. Standard Sieve Series. Preferably, they are from 1 to 40 microns, most preferably from 2 to 20 microns in particle sizes, with distribution of particle sizes being normal over the range. Representative polishing agents include, for example, dicalcium phosphate, tricalcium phosphate, insoluble sodium metaphosphate, aluminum hydroxide, including hydrated alumina, colloidal silica, magnesium carbonate, calcium carbonate, calcium pyrophosphate, bentonite, etc., including suitable mixtures thereof. When employed, it is preferred to use the water insoluble phosphate salts as the polishing agent and more particularly insoluble sodium metaphosphate and/or a calcium phosphate such as dicalcium phosphate dihydrate in dental creams.

The above listing of polishing agents, and other listings of other constituents of the dentifrice composition to be given in the present specification are not intended to be exhaustive and therefore, for other materials of these types reference should be made to a standard handbook, such as *Cosmetics: Science and Technology*, by Sagarin, 2nd printing, 1963, published by Interscience Publishers, Inc. Most of the polishing agents mentioned are most useful in the preparation of opaque dentifrices but some of them, such as the colloidal silicas, especially the silica xerogels, and complex sodium aluminosilicates, such as those sold under the trademark Syloid as Syloid 72 and Syloid 74 or under the trademark Santocel as Santocel 100 and synthetic alkali metal aluminosilicate complexes may be particularly useful, in the manufacture of clear dentifrices, because their indexes of refraction approximate those of the rest of the dentifrice constituents in an appropriate vehicle, i.e., of the gelling agent-liquid (generally including humectants such as glycerine and sorbitol) systems commonly used in dentifrices.

The content of polishing agent in the final dentifrice product is variable, generally being greater for the opaque than for the translucent or transparent dental gels. For example, in the manufacture of commercially acceptable opaque form-retaining, extrudable dental creams there usually will be present about 20 to 75% of polishing agent, e.g., dicalcium phosphate, but in the manufacture of clear dental gels, also form-retaining and extrudable, the content of polishing agent is typically about 5 to 40%. The preferred proportions of such constituents are about 40 to 60% and about 10 to 30%, respectively. In the case of the polishing agent for opaque products, a most preferred composition includes hydrated dicalcium phosphate and anhydrous dicalcium phosphate, with the latter being present to the extent of about 5 to 20% of the total dicalcium phosphate content. With respect to the transparent or translucent dental gels, either sodium aluminosilicate complex or silica xerogel will usually be employed separately, although mixtures thereof may find special advantages in some products where the desired polishing properties may be so regulated. It will be seen that the polishing agents utilized in accordance with the invention are normally water insoluble inorganic metal oxides, hydroxides, salts and hydrates but water insoluble organic compounds may also be employed in substitution thereof, although usually for only minor proportions of the total polishing agent. For example, polyacrylamides, polymethyl methacrylates, polyesters and nylons may be utilized.

Of the water-insoluble polishing agents, most are well known chemical compounds. The complex aluminosilicate salts, which appear to contain interbonded silica and alumina having Al—O—Si bonds, are described by Tamele, in "Chemistry of the Surface and the Activity of Aluminum-Silica Cracking Catalysts", appearing in *Discussions of the Faraday Society*, No. 8, pages 270–279 (1950), particularly at page 273, FIG. 1, Curve 3, and in the article by Milliken et al., entitled "The Chemical Characteristics and Structure of Cracking Catalysts", in *Discussions of the Faraday Society*, No. 8, 279-290 (1950), particularly in the sentence bridging pages 284 and 285. The colloidal silicas used are silica Aerogels. Typically they have a refractive index of about 1.44 to 1.47 and a loose bulk density of about 0.07 to 0.12 g./c. cm. and are of particle sizes of 1 to 20 microns. Appropriate aerogels have been marketed under the trademarks Syloid 63 and Syloid 74.

Organic surface-active agents are used in the compositions of the present invention to assist in achieving thorough and complete dispersion of the instant compositions throughout the oral cavity and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. Suitable such detergents are water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2-dihydroxy propane sulfonates, and the substantially saturated high aliphatic acyl amides of lower aliphatic amino carboxylic acid compounds, such as those having 12 to 16 carbon atoms in the fatty acid, or acyl radicals, and the like. Examples of the last mentioned amides are N-lauroyl sarcosine, and the sodium potassium and ethanolamine salts of N-lauroyl, N-myristoyl, or N-palmitoyl sarcosine which should be substantially free from soap or similar higher fatty acid material which tends to substantially reduce the effect of these compounds. The use of these sarcosinate compounds in the dentifrice compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Other particularly suitable surface active materials include nonionic agents such as condensates of sorbitan monostearate with approximately 20 moles of ethylene oxide, condensates of ethylene oxide with propylene oxide, condensates of propylene glycol ("Pluronics"), and amphoteric agents such as quaternized imidazole derivatives which are available under the trademark "Miranol" such as Miranol $C_2M$.

Other suitable nonionic detergents are the condensation proudcts of an α-olefin oxide containing 10 to 20 carbon atoms, a polyhydric alcohol containing 2 to 10 carbons and 2 to 6 hydroxyl groups and either ethylene oxide or a heteric mixture of ethylene oxide and propylene oxide. The resultant detergents are heteric polymers having a molecular weight in the range of 400 to about 1600 and containing 40 to 80% by weight of ethylene oxide, with an α-olefin oxide to polyhydric alcohol mole ratio in the range of about 1:1 to 1:3. These detergents are manufactured using well-known polymerization techniques under conditions of high temperature and high pressure. The olefin oxide and polyhydric alcohol usually are added to the reactor prior to the addition of ethylene oxide. These nonionic detergents may be mixed with similar nonionic detergents as well as other types nonionic detergents described herein.

There may also be employed olefin sulfonate detergents, typically long chain alkenyl sulfonates.

The α-olefin feedstock preferably contains olefins of 8–25 carbon atoms, most preferably 12–21 carbon atoms. The feedstock may contain minor amounts of other constituents, such as secondary or internal olefins, diolefins, cyclic olefins, armomatics, naphthalenes, and alkanes. Best results have been obtained when α-olefins (where $R_1$ is H) constitute a major proportion. A typical olefin feedstock contains in the range of about 12 to 21 carbon atoms in the molecule and yields olefin sulfonates having excellent detergency properties. Especially good foaming characteristics have been obtained by the use of a feedstock whose α-olefin content consists essentially of compounds of 15 to 18 carbon atoms.

The detergent material above produced typically contains at least about 50% by weight of long-chain alkenyl sulfonate, up to about 33% by weight of hydroxy alkane sulfonate, and up to about 15% of impurities, such as long chain water-insoluble sultones, most of which impurities are characterized as being soluble in acetone.

The olefin sulfonate is generally employed in the form of its sodium salt. It is within the scope of this invention to use other water-soluble salts, for example, salts of other alkali metals such as potassium salts of alkaline earth metals, such as magnesium and calcium, triethanolamine, salts and the like, as well as mixtures of a salt such as a sodium salt with the free olefin sulfonic acid.

It is preferred to use from about 0.05 to 5% by weight of the foregoing surface-activw materials in the instant oral preparations.

Various other compatible and suitable materials may be incorporated in the dentifrice formulatikns of this invention. Examples thereof are coloring or whitening agents or dyestuffs, preservatives, silicones, chlorophyll compounds, ammoniated materials such as urea, diammonium phosphate and mixtures thereof, and other constituents. These adjuvants are incorporated in the instant compositions in amounts which do not substantially adversely affect the properties and characteristics desired and are selected and used in proper amount depending upon the particular type of preparation involved.

The compositions of the present invention may also contain a fluorine-containing compound having a beneficial effect on the care and hygiene of the oral cavity, e.g., diminution of enamel solubility in acid and protection of the teeth against decay. Examples thereof include sodium fluoride, stannous and manganese fluoride, potassium fluoride, potassium stannous fluoride ($SnF_2KF$), potassium fluorozirconate, sodium hexafluorostannate, stannous chlorofluoride, and sodium monofluorphosphate. These materials which dissociate or release fluorine-containing ions, suitably may be present in an effective but non-toxic amount usually within the range of about 0.1 to 1% by weight, based on the water-soluble fluorine content thereof. Sodium fluoride, stannous fluoride, and sodium monofluorophosphate are particularly preferred, as well as mixtures thereof.

Antibacterial agents may also be employed in the oral preparation of the instant invention to provide a total content of such agents of up to about 5% by weight, preferably about 0.01 to 5.0%, most preferably about 0.05 to 1.0%. Typical antibacterial agents include:

$N^1$-(4-chlorobenzyl)-$N^5$-(2,4-dichlorobenzyl) biguanide;
p-chlorophenyl biguanide;
4-chlorobenzhydryl biguanide;
4-chlorobenzhydrylguanylurea;
N-3-lauroxpropyl-$N^5$-p-chlorobenzylbiguanide;
1(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
1,6-di-p-chlorophenyl bigaunidohexane;
1,6-bis(2-ethylhexyl biguanido) hexane;
5-amino-1,3-bis(2-ethylhexyl)-5-methylhexahydropyrimidine;

and their non-toxic acid addition salts.

Synthetic finely divided pyrogenic silica such as those sold under the trademark Cab-O-Sil M-5, Syloid 244, Syloid 266 and Aerosil D-200 may also be employed in amounts of about 1-5% by weight to promote thickening or gelling and to improve clarity of the dentifrice.

The taste of the new compositions may be modified by employing additional suitable flavoring or sweetening materials, which compatible materials may be blended into the dental vehicle along with the other materials heretofore mentioned.

The flavors which may be used include flavoring agents which may be in solid or liquid form. Most of such agents will be essential oils but the flavors may also include various flavoring aldehydes, esters, alcohols and similar materials, often the higher fatty compounds, known in the art. Examples of the essential oils include oils of spearmint, peppermint, wintergreen, sassafras, clove, sage, eucalyptus, marjoram, cinnamon, lemon lime, grapefruit and orange. Also useful are such chemicals as menthol, carvone and anethole. Of these, the most commonly employed are the oils of peppermint, spearmint, and eucaluptus and anethole, menthol and carvone. In some cases flavorful solvents, such as chloroform and mock chloroform, may be employed. Such flavorings may be used as liquids or may be solidified by being mixed with a particulate carrier material, such as starch, calcium carbonate, paraffin, vegetable wax, fat, higher fatty acid or other suitable carrier substances. In the cases of solid flavors, such as vanillin, sage, citric acid or licorice, the flavor may be converted to liquid form, if so desired, by dissolving it in the solvent or emulsifying it, usually with the help of a synthetic or natural emulsifying agent. The choice as to whether to utilize particulate solid or liquid flavors or to convert such flavors to a particulate solid or liquid form, respectively, will often depend on the properties desired in the flavor and its compatibility with the sweetener and any other material to be present with it. Thus, where chemical interactions with the acid anhydride and/or the sweetener are to be avoided it may well be desirable to utilize only solid compatible flavors but in those cases where reactions are not probable or objectionable, liquids may be used. Of course, even in the cases of liquids, the thickness of the liquid may be adjusted by utilization of gelling agents or thickeners, usually to the extent of less than about 10% of the flavor, preferably about 1 to 10% thereof. Similarly, the solid particles will have a viscosity of about 0.1 to 1,000 centipoises, preferably about 0.5 to 10 centipoises and the particle sizes will be about 0.1 micron to 1 millimeter, preferably about 1 to 100 microns in diameters.

The dipeptide sweetener will usually be a minor proportion of the total dentifrice product, preferably about 0.1 or 0.5 to 10% thereof. The acid anhydride will generally be included in amounts of about 0.1 to 15.0%, preferably 0.1 to 1.0% and most preferably 0.25 to 0.5% by weight. Of course, the percentages of adjuvants or other materials also present may be regulated for best results and usually will be about 0.2 to 5 times the weight of the sweetener. The proportion of additional sweetener where desired in the dentifrice or flavor will normally be about 0.1 to 2% of the entire product, preferably about 0.5 to 1.5% thereof.

It is believed that the acid anhydride functions to maintain the acid pH integrity (about 3–5) of the sweetener, help to absorb excess free water present and thereby provide for maximum stability of the sweetener without the occassionally needed step of making major changes in the acidity of the dentifrice vehicle. Suitable acid anhydrides include but are not limited to the food acidulents, such as acetic-, succinic-, adipic-, fumaric-, lactic-, malic acid and the like; vitamin and amino acids, such as folic-, ascorbic-, aspartic-, and the like; antimicrobial acids such as benzoic acid and the like; synthetic flavoring acids, such as isovaleric-, phenoxyacetic acid and the like; chelating acids, such as citric-, tartaric acid and the like; inorganic acids, such as orthophosphoric acid and the like; and fatty acids, such as lauric-, stearic acid and the like; and compatible mixtures thereof. Additional operative examples of the acids falling within the above described groupings may be found in *The Handbook of Food Additives*, published by the Chemical Rubber Company, 1968; the foregoing is incorporated herein in its entirety by reference.

Because the mouth is substantially aqueous environment the flavors utilized will normally be water-soluble, emulsifiable or dispersible.

The invention will appear more fully from the examples which follow. These examples are set forth by way of illustration only and it will be understood that the invention is not to be construed as limited either in spirit or in scope by the details contained therein as many modifications both in materials and methods will be apparent from this disclosure to those skilled in the art. In the examples and the appended claims, quantities of materials are expressed in parts, proportions or percentages by weight except where otherwise noted.

EXAMPLE 1

| EXAMPLE 1 | |
|---|---|
| | Parts |
| Glycerin | 58.69 |
| Carbowax 600 (polyethylene glycol-Union Carbide) | 3.00 |
| Aspartyl phenyl alanine methyl ester | 0.40 |
| Succinic anhydride | 0.50 |
| Benzoic acid | 0.15 |
| Sodium monofluorophosphate | 0.76 |

-continued

| EXAMPLE 1 | |
|---|---|
| | Parts |
| Na Aluminum Silicate | 30.00 |
| Silica Aerogel | 4.00 |
| Na Lauryl Sulfate | 1.50 |
| Flavor | 1.00 |

The above materials are formulated in the usual manner into an extrudible toothpaste.

EXAMPLE 2

Example 1 is repeated with the same materials except that the following variations are made.

In addition to the methyl ester sweetener present at 0.3%, there is also present 1.0% flavor of spearmint and present with the spearmint is about 0.1% of sodium saccharin and 0.02 of green colorant (F.D. & C. Green #3) of the water-soluble type.

EXAMPLES 3-4

The procedure of examples 1 and 2 are repeated, however, the formulations are varied as follows.

| EXAMPLE 3 - DENTAL CREAM | |
|---|---|
| | Parts |
| Syloid 244 | 3.0 |
| Antimicrobial agent | 0.1 |
| Sodium benzoate | 0.15 |
| Aspartylphenylalanine methyl ester | 0.20 |
| Sodium lauryl sulfate | 1.5 |
| Insoluble sodium metaphosphate | 38.6 |
| Dicalcium phosphate dihydrate | 5.0 |
| Titanium dioxide | 0.4 |
| Stannous fluoride | 0.4 |
| Gum tragacanth | 0.4 |
| Oil of wintergreen | 1.0 |
| Color | 0.03 |
| Stearic anhydride | 2.00 |
| Glycerine (99.3%) | 27.10 |

This composition is used by brushing the teeth therewith at least once daily.

In the above dental cream, the sodium lauryl sulfate may be replaced by sodium-N-lauroylsarcosinate.

| EXAMPLE 4-DENTAL CREAM | |
|---|---|
| | Parts |
| Antimicrobial agent | 0.1 |
| Aspartylphenylalanine methyl ester | 0.2 |
| Sodium Benzoate | 0.5 |
| Sodium acid pyrophosphate | 0.25 |
| Cab-O-Sil | 2.00 |
| Dicalcium phosphate dihydrate | 35.25 |
| Calcium carbonate | 5.0 |
| Sodium carboxymethylcellulose | 0.25 |
| Olefin sulfonate | 2.0 |
| Glycerine (99.3%) | 23.95 |
| Oils of peppermint and spearmint, 1:1 | 0.8 |
| Benzoic anhydride | 3.0 |

In other experiments, the flavor(s) are changed to eucalyptus, anethole, menthol and carvone and the proportions are varied over the 0.5 to 5% range, with similar results. Generally, however, the total amount of flavoring employed will be about 0.5 to 2% based upon the total dentifrice, for best taste effects.

EXAMPLE 5

| EXAMPLE 5 | |
|---|---|
| | Parts |
| Glycerine (99.5% C.P.) | 17.0 |

-continued

| EXAMPLE 5 | |
|---|---|
| | Parts |
| Cab-O-Sil | 1.0 |
| Aspartylphenylalanine methyl ester | 1.0 |
| Succinic anhydride | 14.5 |
| Hydrated alumina, (2 to 20 microns in dia.) | 55.0 |
| Sodium N-lauroyl sarcosine | 2.0 |
| Glycerine (99.5% C.P.) | 2.9 |
| Dental cream flavoring (essential oils, sweeteners, esters) | 1.2 |

The above opaque dental cream is made by a method corresponding to that of Example 1.

EXAMPLE 6

The procedure of Example 2 is followed, utilizing the formula given below, to make a clear gel dentifrice.

| Components: | Parts |
|---|---|
| Mannitol | 75.0 |
| Glycerine | 25.0 |
| Laponite SP | 2.0 |
| Sodium N-lauroyl sarcosinate | 2.0 |
| Aspartylphenylaniline methyl ester | 0.1 |
| Aerosil D200 | 3.0 |
| Sodium aluminumsilicate | 16.0 |
| Flavor | 1.0 |
| Color | 1.0 |
| Succinic anhydride | 3.0 |

The sodium aluminumsilicate employed is a complex having a refractive index of about 1.46, a moisture content of about 6 percent, an average particulate size of about 35 microns and a sieve loose bulk density of about 0.07 g./cc.

The various parts of the formulation are blended together in the manner described with respect to the preceding examples.

The product resulting is of excellent clarity and taste and when it has coloring materials such as F.D. & C. Blue #1 added to it, to the extent of 10% of the sweetener, gives a product a distinctive appearance.

EXAMPLE 7

The procedure of Example 1 is followed for the production of a transparent cream.

| | Parts |
|---|---|
| Glycerine | 25.00 |
| Sodium carboxymethylcellulose | 0.70 |
| Aspartylphenylalanine methyl ester | 0.17 |
| Sodium benzoate | 0.50 |
| Sorbitol | 44.83 |
| Benzoic anhydride | 2.0 |
| Sodium aluminum silicate | 16.00 |
| Syloid 244 | 5.00 |
| Flavor | 1.00 |
| Sodium Lauryl sulfate | 2.00 |

The invention has been described with respect to various examples thereof but it is clear that such examples and previously given illustration are not limitative, since one of ordinary skill in the art will be able to employ substitutes and equivalents without departing from the inventive concept.

I claim:

1. An anhydrous dentifrice which contains about 10 to 90% by weight of a liquid vehicle including a hydroscopic humectant, about 0.1 to 10% by weight of a dipeptide sweetener selected from the group consisting of L-aspartyl-L-phenylalanine methyl and ethyl esters and L-aspartyl-L-hexahydrophenylalanine methyl and ethyl esters in admixture with about 0.1 to 15% by weight of a non-toxic acid anhydride selected from the group consisting of acetic-, succinic-, adipic-, fumaric-, lactic-, malic-, folic-, ascorbic-, aspartic-, benzoic-, isovaleric-, phenoxyacetic-, citric-, tartaric-, orthophosphoric-, lauric- and stearic acid anhydride and compatible mixtures thereof whereby the acid pH integrity of acid sweetener is maintained about 3 to 5 and excess-free water present is absorbed thereby providing stability in said sweetener, said dentifrice further including a fluorine compound in an amount having a beneficial but non-toxic effect on the care and hygiene of the oral cavity.

2. A dentifrice as defined in claim 1 wherein said fluorine containing compound is selected from the group consisting of sodium fluoride, stannous fluoride, potassium fluoride, potassium stannous fluoride, sodium hexafluorostannate, stannous chlorofluoride, sodium fluorozirconate, sodium monofluorophosphate and manganese fluoride.

3. A dentifrice according to claim 1 wherein said sweetener is L-aspartyl-L-phenylalanine methylester.

4. A dentifrice as defined in claim 1 further containing an effective amount of an anti-bacterial agent.

5. A dentifrice according to claim 1 wherein said acid anhydride is selected from the group consisting of the food acidulents, vitamin and amino acids, antimicrobial acids, synthetic flavor acids, chelating acids, inorganic acids and fatty acids.

6. A dentifrice according to claim 1 which is a toothpaste comprising a polishing agent.

7. A dentifrice according to claim 6 which comprises about from said 5 to 75% of said polishing agent.

8. A dentifrice according to claim 7 which also includes from 0.5 to 10% of a gelling agent and 0.5 to 5% of a synthetic organic detergent and in which the polishing agent is selected from the group consisting of sodium aluminum silicate, hydrated alumina, dicalcium phosphate silica xerogel and calcium carbonate and mixture thereof, and a vehicle selected from the group consisting of mannitol, sorbitol, glycerine and mixtures thereof, the gelling agent is selected from the group consisting of sodium carboxymethyl cellulose, hydroxyethyl cellulose, polyvinyl alcohol, Irish moss and silica aerogel and mixtures thereof and the synthetic organic detergent selected from the group consisting of water-soluble higher fatty acid salts and synthetic anionic and nonionic detergents.

9. A dentifrice according to claim 8 which contains therein, apart from said sweetener, about 0.1 to 2% of a flavoring material.

10. A dentifrice according to claim 6 additionally containing 0.1 to 3.0% of a further sweetening agent.

11. A dentifrice according to claim 6 additionally containing 0.1 to 10% of a combination of flavoring oils and sweetening agents in said vehicle.

12. A dentifrice according to claim 6 wherein said vehicle also contains a material selected from the group consisting of coloring agents, enzymes, tooth hardening agents, bactericides, and anti-enzymatic compounds.

13. A dentifrice as defined in claim 6 wherein said polishing agent is water-insoluble.

14. A dentifrice as defined in claim 6 wherein said polishing agent is about 20–95 percent by weight of the vehicle.

15. A dentifrice as defined in claim 1 additionally containing a surface-active agent.

16. A dentifrice as defined in claim 15 wherein said surface-active agent is selected from the group consisting of water-soluble sulfates of compounds having long chain alkyl radicals and α-olefin sulfonates.

17. A dentifrice according to claim 14 in clear gel form, containing a polishing agent of approximately the same index of refraction as the balance of the dentifrice.

* * * * *